United States Patent
Liu et al.

(10) Patent No.: US 8,617,579 B2
(45) Date of Patent: Dec. 31, 2013

(54) PRE-BLENDED MIXTURES OF SPECIFIC NATURALLY SOURCED LIQUID MATERIALS STRUCTURED WITH NATURALLY SOURCED HIGH MELTING POINT STRUCTURING MATERIAL

(75) Inventors: Hongjie Liu, Trumbull, CT (US); Yuntao Thomas Hu, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/447,350

(22) Filed: Apr. 16, 2012

(65) Prior Publication Data

US 2013/0272988 A1 Oct. 17, 2013

(51) Int. Cl.
*A61Q 1/04* (2006.01)
*A61Q 1/06* (2006.01)

(52) U.S. Cl.
USPC ............................................. 424/401; 424/64

(58) Field of Classification Search
None
See application file for complete search history.

(56) References Cited

U.S. PATENT DOCUMENTS

| 5,869,070 | A | | 2/1999 | Dixon et al. |
| 6,033,680 | A | | 3/2000 | Dixon et al. |
| 6,045,782 | A | * | 4/2000 | Krog et al. ...................... 424/64 |
| 6,066,316 | A | * | 5/2000 | Shiojima et al. ........... 424/70.19 |
| 6,521,573 | B2 | | 2/2003 | Tsaur et al. |
| 7,615,237 | B1 | * | 11/2009 | Takada et al. ................. 424/449 |
| 7,776,346 | B2 | | 8/2010 | O'Connor et al. |

FOREIGN PATENT DOCUMENTS

WO WO9909950 3/1999

OTHER PUBLICATIONS

Co-Pending U.S. Appl. No. 13/447,343; titled Pre-Blended Mixtures of Specific Hydrocarbon Liquids Structred With High Melting Point Structuring Material.

* cited by examiner

*Primary Examiner* — Susan Tran
(74) *Attorney, Agent, or Firm* — Ronald A. Koatz

(57) ABSTRACT

The invention provides pre-blended mixtures of specific naturally sourced liquid materials of defined viscosity structured with naturally sourced high melting point materials.

6 Claims, No Drawings

PRE-BLENDED MIXTURES OF SPECIFIC NATURALLY SOURCED LIQUID MATERIALS STRUCTURED WITH NATURALLY SOURCED HIGH MELTING POINT STRUCTURING MATERIAL

FIELD OF THE INVENTION

The present invention relates to novel pre-blended mixtures of specific naturally sourced liquid materials of defined viscosity structured with naturally sourced high melting point materials, e.g., waxes. These pre-blends provide occlusivity (e.g., moisture retention) which approach or equal that of petrolatum, an objective not easily obtained. In this regard, the materials can be used as substitutes for petrolatum. The mixtures can be used as stand-alone blends for use in a variety of personal care compositions (e.g., personal wash, hair care) and/or they can be blended in separate mixers as part of overall process when making the above-noted products. In applicants' separately filed co-pending application, applicants claim mixtures wherein it is not required that either the base liquids or the structuring agent be non-petroleum derived. By contrast, both liquids of the subject invention and structuring agent are derived specifically from naturally sourced materials (by naturally sourced, we refer to non-petrolatum based materials).

BACKGROUND

Petrolatum is a colorless or pale yellow semi-solid material comprising a mixture of hydrocarbons and which is often used in cosmetic and personal care products (e.g., cleansing products, skin-care products, make-up, shampoos and conditioners, shaving products, suntan products). For example, it can function as hair conditioning agent, skin protectant, occlusive skin-conditioning agent, etc.

It is extremely difficult to find alternative products which are similar to and/or function equivalently to petrolatum. Unexpectedly, applicants have now found materials (structured, pre-blended mixtures) and methods (i.e., formation of said pre-mixtures) to approach or match some of the properties (e.g., occlusivity) of petrolatum while retaining rheological characteristics. The present invention is directed to pre-blends in which the liquid materials (used as base of the pre-blend), as well as the structuring agents, are naturally sourced materials (non-petroleum sourced materials). In a related co-pending application, applicants claim pre-blends in which the base liquids and/or the structuring agents used may be more broadly petroleum or non-petroleum derived materials.

As noted, applicants have unexpectedly now found that a pre-blend of specific non-petroleum based liquid materials (e.g., squalane, squalene, natural rubber) of defined viscosity and defined melting or phase transition point, together with non-petroleum based structuring materials of defined melting point, can be used instead of petrolatum. (e.g., petrolatum jelly or "PJ"); and will approach or match the occlusivity of PJ, while also providing spreadability required to achieve the film forming and sensory profile desired by consumers. As "natural" materials, they may also have greater appeal to some consumers.

Various references disclose compositions where waxes, for example, are disclosed and/or polymers/oligomers are disclosed; but no reference of which applicants are aware discloses a pre-blend where specific materials (i.e., specifically selected to have melting or phase transition point below 30° C.; and a viscosity of 500 Pa·s of below at room temperature) are pre-blended with specific high melting point materials, either for use as separate component (stand-alone blends for use as ingredients) or, optionally, before combining with other compositional ingredients during preparation of personal care compositions.

U.S. Pat. No. 5,869,070 and U.S. Pat. No. 6,033,680, both to Dixon et al., disclose dual cleanser moisturizer compositions which may comprise mixtures of petrolatum with the types of oil used in our invention (e.g., polybutene) at defined ratios of petrolatum to the hydrocarbon oils (col. 7, lines 5-12); and/or where wax alone is disclosed (e.g., col. 6, line 60), but nowhere is there disclosed mixture (particularly where pre-blended) of wax or other high melting point ingredients and liquid materials to form the structured pre-blended mixtures of our invention.

WO 99/09950 to Elliott et al. (P&G) discloses the use of certain branched polymers, as well as, broadly, possible use of waxes. However, nowhere is there recognized specifically preparing a pre-blend to obtain the materials disclosed in our invention.

U.S. Pat. No. 6,521,573 to Tsaur et al. also discloses generally the use of hydrocarbon polymers and hydrophobic oils. There is no mention of wax and certainly no suggestion of pre-blending specifically selected liquid materials (having viscosity of 500 Pa·s or below and melting or glass transition point of <30° C.); and high melting point structuring materials to produce the pre-blends of our invention.

U.S. Pat. No. 7,776,346 to O'Connor et al. discloses oils which may be structured with certain crystalline materials. There is no disclosure of the specific materials of our invention pre-blended with high melting point materials to unexpectedly obtain pre-blends which approach or match occlusivity, while retaining rheological characteristics (spreadability, feel) of petrolatum.

In short, applicants are aware of no references which teach or suggest the unique naturally sourced liquid materials and naturally sourced structuring materials of our invention pre-blended to form the mixtures of our invention, i.e., mixtures which provide the unexpected advantage of approaching or matching occlusivity, while retaining rheological characteristics (spreadability) of petrolatum. Petrolatum is a very unique material and obtaining functional equivalents is not a readily achievable goal.

BRIEF DESCRIPTION OF THE INVENTION

In one embodiment, the present invention relates to specific premix compositions which provide an occlusivity which approaches or equals that of petrolatum while simultaneously retaining rheological characteristics (spread, feel) of petrolatum.

These pre-blends are made by mixing a base or continuous phase comprising specific liquid materials with specific natural structuring agents. Examples of materials which can be used as (1) the base liquid phase and (2) as the structuring agent are summarized below.

Example of materials which can be used in base/continuous phase include natural hydrocarbon, such as natural rubber, squalane and squalene.

Examples of naturally-based structuring agents include (1) naturally derived animal waxes (e.g., beeswax, lanolin, shellac); (2) naturally derived plant and vegetable waxes (e.g., candelilla wax, castor wax, jojoba oil); (3) naturally derived animal fat; and (4) naturally derived fatty acids (preferably $C_{16}$-$C_{40}$ chain length) and/or fatty alcohol.

More specifically, pre-blended mixture compositions of the invention comprise:

(a) 25 to 95%, preferably 40 to 90% by wt. of naturally derived hydrocarbon liquids including oligomers and polymers having two or more isoprene units (e.g., squalene), although saturated natural alkenes (e.g., squalane) are also contemplated; and natural rubbers;

(b) wherein the hydrocarbon liquids of (a) have a melting or glass transition point <30° C. such that they are flowable (viscosity 500 Pa·s or below) at room temperature (about 20-25° C.) and (c) 5 to 75%, preferably 10 to 60% by wt. of naturally derived structuring materials for the hydrocarbon liquids selected from the group consisting of naturally derived animal waxes, naturally derived plant and vegetable waxes; naturally derived animal fat; and naturally derived fatty acids and/or fatty alcohols, wherein these materials have melting point above 30° C., preferably above 35° C. and more preferably above 45° C.; among materials which may be used are included animal waxes (e.g., beeswax, lanolin, shellac, Chinese wax); animal fat (tallow); botanic and vegetable waxes (e.g., candelilla wax, jojoba esters, carnauba wax, Japanese wax, rice bran wax, soy wax, castor wax, bayberry wax, ouricury wax, etc.), wherein the pre-blended mixtures have viscosity from 1 Pa·s to 1000 Pa·s, preferably 5 to 500 Pa·s when measured at shear rate of $10s^{-1}$ at 25° C.; and an occlusivity of >40, preferably >50, more preferably >80.

Even when occlusivity of the blend is low 40 range, the occlusivity is 50% or more, preferably 100% or more, more preferably 150% or more and even more preferably 200% or more (i.e., two times or more) higher in occlusivity compared to the base alone.

While claims of co-pending application are directed to blends where hydrocarbon oils may be petroleum or non-petroleum derived materials as hydrocarbon liquid base phase or structuring agent, claims of subject application are specifically directed to blends where the both continuous, phase and structuring agent are non-petroleum derived materials.

When liquid materials of the invention (e.g., squalane oil) are pre-blended with structuring materials in a pre-mix, they approach or match the intrinsic occlusivity of petrolatum (i.e., are excellent moisturizers) while also retaining the rheology (e.g., spreadability) of petrolatum. It is an unexpected advantage to produce such blends using any materials. It is particularly advantageous to make such materials from so-called natural materials (i.e., non-petroleum derived). Blends prepared from these specific natural materials are claimed in the subject application.

In a second embodiment, the invention relates to a method of obtaining pre-blended materials approaching or matching the occlusivity of petrolatum while retaining rheology of petrolatum which method comprises pre-blending specifically selected naturally-sourced liquid materials with specific naturally sourced high melting point structuring materials to form pre-blends of defined viscosity as defined above.

In a third embodiment, the invention relates to a method of providing petrolatum-like rheology and moisturized feel (to people in need for such moisturized feel) to skin or other desired substrate which method comprises applying to such skin or substrate specific combination of ingredients noted above which have been pre-blended. The pre-blends may be applied directly or, optionally, mixed into personal care compositions (subsequent to having been specifically prepared as a pre-blend).

In Table 1 and in the Examples, applicants show various examples of pre-blend compositions comprising naturally sourced liquid bases and naturally sourced structuring agents.

The occlusivities of the pre-blends prepared by the process of the invention are much higher than those of the bases alone or those of simple blends made by merely combining ingredients; and occlusivities can approach or match the occlusivity of petrolatum.

Blend 1 in examples shows that a pre-blend having. 80% wt. naturally occurring hydrocarbon (polyisoprene, also known as natural rubber) and 20% wt. natural plant wax (candelilla wax) gives occlusivity which relates that of petrolatum.

Blend 2 in examples shows that a pre-blended mixtures of olive oil based hydrocarbon (squalane) and natural sourced candelilla wax has occlusivity which approaches that of petrolatum.

Blends 3 to 5 show the pre-blended mixtures of natural liquid hydrocarbon (squalane) with different structuring waxes that all significantly improve the occlusivity compared to that of squalane alone.

DETAILED DESCRIPTION OF THE INVENTION

In one embodiment, the present invention relates to novel, unique pre-blended materials which allow for use of specific structured, naturally sourced liquid materials. These pre-blended mixtures approach or equal the moisturizing properties (occlusivity) and simultaneously retain rheological properties (spreadability) of petrolatum.

Specifically, the premix is made by blending the following two materials:

(a) 25 to 95%, preferably 40 to 90% by wt. specific naturally derived hydrocarbon liquids such as oligomers, and polymers having two or more isoprene units, saturated natural alkenes (e.g., squalene), and natural rubbers; (specific non-petroleum materials are claimed in co-pending application);

(b) wherein the hydrocarbon liquids of (a) have a melting or glass transition point <30° C. such that they are flowable; by flowable is meant they have viscosity of 500 Pa·s or below at room temperature; and (c) 5 to 75%, preferably 10 to 60% by wt. of naturally derived structurants for the hydrocarbon liquids selected from the group consisting of naturally derived animal waxes, naturally derived plant and vegetable waxes; naturally derived animal fats; and naturally derived fatty acids and/or fatty alcohol; wherein the structuring materials have a melting point above 30° C., preferably above 35° C., and more preferably above 45° C.;

wherein the pre-blended mixtures have viscosity of 1 to 1000 Pa·s, preferably 5 to 500 Pa·s, measured at shear rate of $10s^{-1}$ at 25° C. and an occlusivity of >40, preferably >50, more preferably >80.

Further occlusivity of blend is 50% or more, preferably 100% or more, more preferably 150% or more, and even more preferably 200% or more greater than occlusivity of base alone.

Naturally Derived Hydrocarbon Liquids

The hydrocarbon liquids of the invention are natural, non-petroleum derived materials (petroleum or non-petroleum derived materials, more generally, are claimed in co-pending application).

In order to make a spreadable pre-blend using the solid, high melting point structuring ingredients of our invention, the hydrocarbon materials used as the base or continuous phase of our invention must be in liquid form at room temperature. Materials used include, but are not limited to, certain oligomers and/or polymers. The oligomers and/or polymers preferably include two or more isoprene units (e.g., squalene). Saturated hydrocarbon-containing branched molecules (e.g., squalane) can also be used. Also contemplated are natural rubbers. What is important is that the molecule be flowable around room temperature, i.e., has viscosity of 500 Pa·s or less.

As noted, the material must be flowable. Specifically, material must have melting or glass transition point <30° C. such that they are flowable at room temperature (measured at 20-25° C.) with the viscosity at room temperature of 500 Pa·s or below.

The hydrocarbon liquids comprise 25 to 95%, preferably 40 to 90% by wt. of the pre-blend.

Naturally Derived Structuring Materials

The structuring materials of the invention may comprise naturally derived animal waxes; naturally derived plant and vegetable waxes; naturally derived animal fats; and naturally derived fatty acids and/or alcohols wherein melting point of said structuring material is greater than 30° C., preferably greater than 45° C.

Among waxes which may be used are animal waxes, such as for example beeswax. Other naturally derived animal waxes include Chinese wax (produced by ceroplastes ceriferus), earwax, lanolin, shellac wax and spermaceti.

Also included are various naturally derived plant and vegetable waxes such as candelilla wax, bayberry wax, carnauba wax, castor wax (e.g., hydrogenated castor oil), Japan wax (a vegetable triglyceride), jojoba oil, ouricury wax, rice bran wax and soy wax. Preferred waxes include soy wax and candelilla wax.

Other materials which may be used as naturally-derived structuring material include animal fat (tallow) and, as noted, naturally-derived long chain ($C_{16}$-$C_{40}$, preferably $C_{16}$-$C_{24}$) fatty acids, fatty alcohols and esters.

Specific examples of premix blends include high viscous hydrocarbons such as natural rubber mixed with, for example, relatively low level (e.g., 20% by wt.) of a wax; or low viscous hydrocarbon (e.g., squalane with molecular weight <2000) with relatively high level (e.g., 50% by wt.) of a wax. It should be noted that, if levels of structurant become too high (e.g., above 75%), the spreadability/rheology of the blend may become readily compromised. A range of 20 to 50% structuring material is particularly preferred.

Pre-Blend Processing

A further critical aspect of the invention is that the naturally derived liquid materials and naturally derived structuring materials must be pre-blended. Pre-blends are prepared by mixing all the ingredients together at temperature 10-20° C. higher than the highest melting point of any ingredient being blended (e.g., typically this is the structuring material such as wax), typically about 80° C. The pre-blends are mixed (e.g., with overhead mixer) at speed of about 500-1500 revolutions per minute (rpm) for about 20-30, preferably 20-40 minutes until completely mixed. Heating is discontinued and mixing is continued until pre-blends are cool at room temperature.

The pre-blended mixture of naturally derived liquid materials and naturally derived structuring materials needs to be mixed by the claimed process in order to provide advantageous properties. The non pre-blended mixture of those materials is not homogeneous and could not even form a uniform film for measurement, let alone obtain the claimed benefit.

Composition

The pre-blended mixtures of the invention may be used, optionally, in personal wash or hair care compositions. For examples, they may be used in a liquid composition comprising:

1) 0 to 99%, preferably 1 to 75%, more preferably 3 to 50% by wt. of a surfactant (e.g., anionic, amphoteric, nonionic or cationic surfactant and mixtures thereof);
2) optional ingredients typically found in liquid personal cleanser for skin or hair; and
3) balance water.

Optional ingredients in personal wash cleanser may include oils (e.g., vegetable oils such as castor oil); esters such as cetyl palmitate; animal fats such as lanolin; fatty acids and alcohols; and other oils-emollients such as mineral oils petrolatum, silicone oil.

Further may be included fatty acids which help form lamellar phase, as well as cationic conditioning agent.

Other optional ingredients which may be used in liquid cleansers include organic solvents (e.g., ethanol); thickeners (e.g., carboxymethyl cellulose); perfumes; sequestering agents; opacifiers; pearlizers; antimicrobials; suds booster (e.g., alkanolamides); antioxidants; thickeners; exfoliants, etc.

Hair compositions may be, for example, shampoos or conditioners. Shampoos may further comprise, in addition to surfactant, cationic polymers; suspending agents (e.g., polyacrylic acids). Conditioners may comprise cationic conditioning surfactants; silicone conditioning agents, fragrances, dyes, pigments, pH adjustment agents, pearlecers, viscosity modifiers, preservatives and antimicrobials.

In another embodiment, the invention relates to method of obtaining premixtures approaching, matching or surpassing occlusivity of petrolatum while maintaining applicable rheology property (e.g., spreadability, feel) which method comprises pre-blending specific liquid materials (as defined above) of defined viscosity with specific concentration of high melting point materials also defined above.

In a third embodiment, the invention relates to a method of providing moisturization (e.g., occlusivity) to skin or other substrate, while retaining rheology of petrolatum, which method comprises applying to substrate a pre-blend of specific liquid materials and structuring materials noted above either directly as pre-blend product or as composition comprising said pre-blend.

Protocol

We define water occlusivity as the inverse of water flux through the occlusive film for a dosage of 1 $g/cm^2$, and as having the unit of $(g/m^2 \cdot hr)^{-1}$. The water occlusivity of pre-blends was measured using the AquaFlux® evaporimeter from Biox (LSBU). The preblends were dosed onto a porous supporting membrane to form a film. The equilibrium water (vapor) fluxes for different dosage were measured (TEWL reading). According to Fick's law, the reverse of water flux linearly depends on the film thickness (also dose for the same material) and the numerical value of the slope represents the average occlusivity.

The spreadability was evaluated by finger/hand palm rubbing of measured by viscometer using the standard methods as defined (ASTM D445, D2270, D937, D1321).

EXAMPLES

Table 1 below shows five examples of pre-blends. Examples of blend 2 and blend 5 specifically comprise natural derived materials as both base and structuring agent. In all cases, the occlusivities of the blends is much higher than those of the bases alone and some of them approach or match the occlusivity of petrolatum.

| base/<br>continuous<br>phase | structuring<br>agent | occlusivity<br>of base<br>(gram/<br>m² · hr)⁻¹ | occlusivity<br>of blend<br>(gram/<br>m² · hr)⁻¹ |
|---|---|---|---|
| Petrolatum | — | — | 148 ± 44 |
| Blend 1 | 80% Natural<br>Rubber<br>(DPR ® 40) | 20% Candelilla<br>wax | 30 ± 2 | 154 ± 30 |
| Blend 2 | 50% Squalane | 50% Candelilla<br>wax | 15 ± 1 | 99 + 1 |
| Blend 3 | 50% Squalane | 50% Hydro-<br>genated soy | 15 ± 1 | 48 ± 2 |
| Blend 4 | 50% Squalane | 50% Carnauba<br>wax | 15 ± 1 | 41 + 7 |
| Blend 5 | 50% Squalane | 50% Jojoba<br>wax | 15 ± 1 | 40 + 8 |

In blend 1, applicants prepared a pre-blend of natural rubber (DPR40®) (liquid base) and 20% candelilla wax. DPR® 40 (DPR Industries) is a liquid natural polyisoprene polymer having an average molecular weight of 32000 and a viscosity of 40 Pa·s at 38° C. As seen in the Table 1, the occlusivity of the pre-blend is much higher than that of lDPR40® alone and matches that of petrolatum.

In blends 2 to blend 5, applicants prepared a pre-blend of 50% olive oil based liquid hydrocarbon squalane and 50% different naturally derived waxes including candelilla wax, hydrogenated soy, carnauba wax and jojoba wax. As seen in Table 1, the occlusivity values of all the pre-blends are much higher than that of squalane alone. Specifically, blend 2 having 50% squalane and 50% candelilla wax has an occlusivity that approaches that of petrolatum.

It is emphasized that all the pre-blends have a spreadable viscosity at room temperature. While hot wishing to be bound by theory this is believed to be the case at least in part because the level of structurant is not too high (e.g., above 75%).

COMPARATIVE EXAMPLES A-F

For blends of Comparative Examples A-F, applicants prepared mixtures of triglyceride oil (e.g., soybean oil) based pre-blends. As seen in Table 2, for all the pre-blended mixtures containing same types of structuring waxes and wax concentrations, the occlusivity values of soybean oil based pre-blends are significantly lower than that of liquid hydrocarbon (e.g., squalane) based pre-blends. For example, blend B in Table 2 containing 50% soybean oil and 50% hydrogenated soy has much lower occlusivity than that of blend 3 in Table 1 which comprises 50% hydrocarbon squalane and 50% candelilla wax.

Blend C containing 20% soybean oil and 80% hydrogenated soy does not have spreadable viscosity at room temperature. This is believed to be due at least in part to the fact that the level of structuring agent is so high.

These examples demonstrate that the selection of hydrocarbon base is critical to the occlusivity of the disclosed blends.

TABLE 2

| base/<br>continuous<br>phase | structuring agent | occlu-<br>sivity<br>of base | occlu-<br>sivity<br>of blend |
|---|---|---|---|
| Petrolatum | — | — | 148 ± 44 |
| Comparative<br>Blend A | 75% soybean<br>oil | 25% Hydrogenated<br>soy | 6 ± 2 | 16 + 1 |
| Comparative | 50% soybean | 50% Hydrogenated | 6 ± 2 | 19 + 1 |

TABLE 2-continued

| base/<br>continuous<br>phase | structuring agent | occlu-<br>sivity<br>of base | occlu-<br>sivity<br>of blend |
|---|---|---|---|
| Blend B | oil | soy | | |
| Comparative<br>Blend C | 20% soybean<br>oil | 80% Hydrogenated<br>soy | 6 ± 2 | 61 + 8 |
| Comparative<br>Blend D | 75% soybean<br>oil | 25% Candelilla wax | 6 ± 2 | 37 + 3 |
| Comparative<br>Blend E | 50% soybean<br>oil | 50% Candelilla wax | 6 ± 2 | 27 + 5 |
| Comparative<br>Blend F | 80% soybean<br>oil | 20% Beeswax | 6 ± 2 | 18 + 4 |

The invention claimed is:

1. Pre-blended mixture composition consisting of:
   (a) 25-95% by wt. of pre-blended mixture composition of naturally derived hydrocarbon liquids selected from the group consisting of (1) squalane; (2) natural rubbers; and (3) mixtures thereof; wherein said hydrocarbon liquids have a melting or phase transition point <30° C. and a viscosity of 500 Pa·s or less at room temperature; and
   (b) 5 to 75% by wt. of pre-blended mixture composition of naturally derived structuring material selected from the group consisting of naturally derived animal waxes; naturally derived plant and vegetable waxes; naturally derived animal fats; naturally derived fatty acids and/or fatty alcohols; and mixtures thereof wherein said structuring material has melting point >30° C.,
   wherein said pre-blended mixture composition comprises flowable hydrocarbon liquid materials (Component a) structured with materials of (b);
   wherein the said pre-blended mixture composition has viscosity below 1000 Pa·s measured at shear rate 10 s⁻¹;
   wherein the pre-blended mixture composition has occlusivity of greater than 40; and
   wherein said pre-blended mixture composition is prepared by mixing (a) and (b) at 500-1500 rpm until completely mixed at temperatures of higher than highest melting point of any ingredient being blended and cooling to room temperature to form the pre-blended mixture composition.

2. A composition according to claim 1 wherein said naturally derived structuring agent comprises Candelilla wax.

3. A composition according to claim 1 wherein components (a) and (b) are mixed at temperature of about 80° C. for 20-60 minutes prior to cooling.

4. A method for obtaining a pre-blended mixture composition having occlusivity of greater than 40 and viscosity of less than 1000 Pa·s at 10 s⁻¹ which comprises making a pre-blended mixture composition as defined by components (a) and (b) of claim 1.

5. A method according to claim 4, wherein said pre-blended mixture composition is prepared by mixing (a) and (b) at 500-1500 rpm until completely mixed at temperature higher than highest melting point of any ingredient being blended and cooling to room temperature to form said pre-blended mixture composition.

6. A method of providing occlusivity values from a pre-blended mixture composition comprising components (a) and (b) below which values are closer to the occlusivity values of petrolatum compared to occlusivity values obtained using pre-blended mixture compositions where components (a) and/or (b) differ from below, wherein said method comprises applying to skin or other substrate the specific pre-blended mixture composition of claim 1 consisting of:

(a) naturally derived hydrocarbon liquids having melting point <30° C. and room temperature viscosity less than 500 Pa·s and wherein said hydrocarbon liquid is selected from the group consisting of (1) squalane; (2) natural rubbers; and (3) mixtures thereof; and
(b) structuring material selected from the group consisting of naturally derived animal waxes, naturally derived plant and vegetable waxes; naturally derived animal fats; naturally derived animal fasts; naturally derived fatty acids and/or alcohols; and mixtures thereof wherein said structuring material has melting point >30° C.

* * * * *